United States Patent [19]

Bruno

[11] Patent Number: 5,332,852
[45] Date of Patent: Jul. 26, 1994

[54] 1,4-O-METALLATION PROCESS

[75] Inventor: Salvatore A. Bruno, Wilmington, Del.

[73] Assignee: E. I. Du Pont de Nemours and Company, Wilmington, Del.

[21] Appl. No.: 713,531

[22] Filed: Jun. 3, 1991

Related U.S. Application Data

[60] Continuation-in-part of Ser. No. 266,891, Nov. 3, 1988, abandoned, which is a division of Ser. No. 727,813, Apr. 26, 1985, abandoned.

[51] Int. Cl.$^5$ .......................... C07F 7/08; C07F 7/10; C07F 7/18
[52] U.S. Cl. .................................. 512/446; 512/413; 512/415; 512/443; 512/444; 556/495; 549/215
[58] Field of Search ............... 556/446, 443, 444, 445, 556/413, 415; 549/214

[56] References Cited

U.S. PATENT DOCUMENTS

| | | | |
|---|---|---|---|
| 2,721,873 | 10/1955 | MacKenzie | 260/488.2 |
| 2,917,530 | 12/1959 | Bailey | 260/488.2 |
| 3,890,359 | 5/1975 | Chandra | 260/429 |
| 4,064,154 | 12/1977 | Chandra et al. | 260/488.2 |
| 4,098,808 | 7/1978 | Wolfers et al. | 556/446 |
| 4,414,376 | 11/1983 | Siedle | 528/15 |
| 4,448,980 | 5/1984 | Sogah | 556/446 |
| 4,482,729 | 11/1984 | Ishikawa et al. | 556/446 |
| 4,503,160 | 8/1983 | Williams | 502/158 |
| 4,780,554 | 10/1988 | Quirk et al. | 556/446 X |
| 4,783,543 | 11/1988 | Schulz et al. | 556/446 |

FOREIGN PATENT DOCUMENTS

| | | | |
|---|---|---|---|
| 1044448 | 9/1966 | United Kingdom | 556/446 U X |
| 1419769 | 12/1975 | United Kingdom | 556/446 U X |
| 1420928 | 1/1976 | United Kingdom | 556/446 U X |
| 1421136 | 1/1976 | United Kingdom | 556/446 U X |

OTHER PUBLICATIONS

Rylander, *Organic Synthesis With Noble Metal Catalysts*, Academic Press, New York & London 1973, pp. 60–65.

Organometallic Chemistry Review A, 6 (1970), pp. 355, 382–390.

Journal of General Chemistry (USSR) 29:2896–2899 (1959), "The Addition of Silicohydrocarbons to $\alpha$,-$\beta$-unsaturated acids and their esters," Petrov et al.

Chem. Pharm. Bull. vol. 22, No. 11:2767–2769 (1974), "Hydrosilation of $\alpha$,$\beta$-Unsaturated Esters," by Yoshii et al.

Journal of American Chemical Society, vol. 79:974–979 (1957) "The Addition of Silicon Hydrides to Olefinic Double Bonds, Part II. The Use of Group VIII Metal Catalysts," Speier et al.

Journal of American Chemical Society, vol. 79:2674–2769 (1957), "Aliphatic Organo-functional Siloxanes, V. Synthesis of Monomers by Platinum-catalyzed Addition of Methyldichlorosilane to Unsaturated Esters and Nitriles." Sommer et al.

Tetrahedron Letters No. 49:5035–5038 (1972), "Selective Reduction of $\alpha$,$\beta$-unsaturated Terpene Carbonyl Compounds Using Hydrosilane-Rhodium (1) Complex Combinations." Ojima et al.

Synthesis (1977), pp. 91–110, "O–Silylated Enolates-- Versatile Intermediates for Organic Synthesis." Rasmussen.

Synthesis (1983), pp. 1–28, "Silyl Enol Ethers in Synthesis-Part I," Brownbridge.

*Primary Examiner*—Paul F. Shaver
*Attorney, Agent, or Firm*—Charles E. Feeny

[57] ABSTRACT

This invention resides in a process for production of predominantly a 1,4-O-metallation product of a hydride of silicon, germanium, or tin with an $\alpha$,$\beta$-unsaturated carbonyl compound. The reaction involved takes place in the presence of a heterogeneous noncomplexed rhodium-containing catalyst. This invention also resides in 1,4-O-metallation compositions having perfluoroalkyl R groups on either side of the C=C bond of an enol ether or on the acetal side of the C=C bond of a ketene acetal.

16 Claims, No Drawings

1,4-O-METALLATION PROCESS

This application is a continuation-in-part of application Ser. No. 07/266,891, filed Nov. 3, 1988, now abandoned, which is a division of application Ser. No. 727,813, filed Apr. 26, 1985, now abandoned.

TECHNICAL FIELD

This invention relates to a process for the preparation of 1,4-O-metallation products from the reaction of $\alpha,\beta$-unsaturated carbonyl compounds with hydrides of silicon, in the presence of a heterogeneous noncomplexed rhodium-containing catalyst. It also relates to certain 1,4-O-metallation compositions wherein some specified R groups are perfluoroalkyl.

BACKGROUND AND SUMMARY OF THE INVENTION

The object of this invention is to produce a 1,4-O-metallation product of the general structure (C) by reacting an $\alpha,\beta$-unsaturated carbonyl compound (i.e., an ester, ketone or aldehyde) of the general structure (B) with a hydride of silicon, of the general structure (A) in the presence of a heterogeneous noncomplexed rhodium-containing catalyst. The process involves the following single step reaction in which the carbon and oxygen positions are numbered.

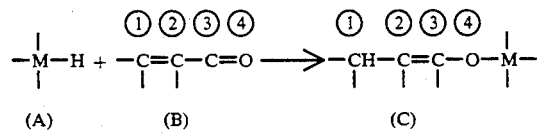

The reaction can be carried out in a solvent or neat, can be run with or without a polymerization inhibitor, can be run at mild reaction conditions (temperatures ranging from about 10° C. to about 75° C. and pressures from about atmospheric to about 20 psig), and yields a high purity product from which the catalyst can easily be separated for recovery or reuse.

The 1,4-O-metallation products, namely enol ethers of the form

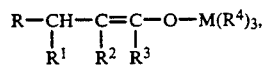

and ketene acetals of the form

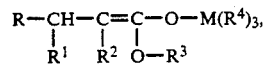

and of the form

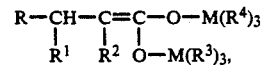

wherein M is silicon, are a useful class of compounds. They are reagents of choice in a wide range of reactions, including those which do not involve carbon-carbon bond formation, heterolytic reactions with carbon-carbon bond formation and pericyclic reactions. Some of these compounds are particularly useful as initiators in the manufacture of polymers for lacquers, oils or rubbers. See U.S. Pat. No. 4,417,034 issued to O. W. Webster on Nov. 22, 1983, and U.S. Pat. No. 4,508,880 issued to O. W. Webster on Apr. 2, 1985.

Compounds of the general structure

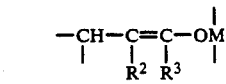

wherein M is silicon, and either $R^2$ or $R^3$ or both $R^2$ and $R^3$ are perfluoroalkyl and compounds of the general structure

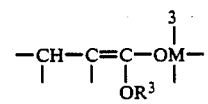

wherein M is silicon, $R^3$ is perfluoroalkyl and no other R group is perfluoroalkyl are new compounds which can be synthesized by the process of this invention.

This invention is also useful for the production of 1,4-O-metallation polyfunctional initiators to be used in making higher molecular weight polymers than would be possible with 1,4-O-metallation products of the form shown above. These polyfunctional initiators are of the form

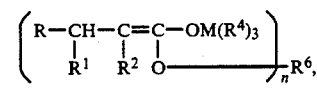

wherein M is silicon.

Representative of the 1,4-O-metallation products and processes for making them is the 1,4-O-silylated product, wherein M is silicon. In the past this type product has been synthesized by one of three methods—the silylation route, the enolate route, and the hydrosilylation route.

The silylation route is described by Rhone-Poulenc S.A. in its British Patent No. 1,044,448. They describe the silylation of an organic compound in the presence of a nickel catalyst. The organic compound must contain an enolizable carbonyl group but be free from other functional groups which are reactive under the reaction conditions. The reaction is accompanied by the evolution of hydrogen, and may be represented as follows:

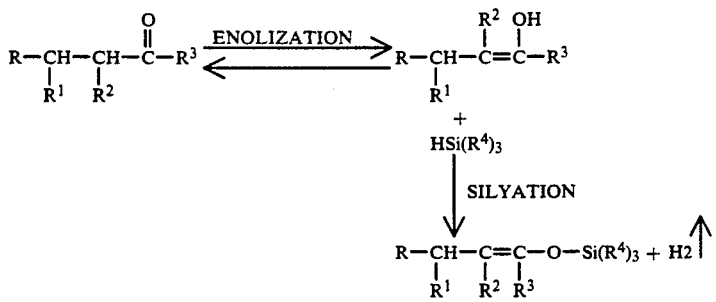

The reaction taught in the British Patent is limited to enolizable aldehydes and ketones. It also involves the evolution of hydrogen.

The enolate route is a three-step reaction which involves the following:
1. Generation of lithium diisopropylamide (LDA),
2. Reaction of the LDA in an organic solvent with the appropriate carbonyl compound to form the enolate, and
3. Reaction of the enolate with a halosilane to form the silylated product.

To isolate the silylated product prepared by the enolate route, filtration to remove salts, evaporation of solvent and distillation of the product are necessary. The process uses large quantities of flammable solvent and a pyrophoric material n butyl lithium to generate LDA. Also, the process suffers from low volumetric efficiencies (less than about 0.5 pound of product per gallon of raw materials) and it must be run at low temperatures (typically less than 0° C.).

The hydrosilylation route involves the reaction of silicon hydrides with $\alpha,\beta$-unsaturated carbonyl compounds. Reaction products of the hydrosilylation can be 1,2 $\alpha$-silylated products, 1,2 $\beta$-silylated products, 3,4-O-silylated products, or 1,4-O-silylated products.

MacKenzie, et al., describe the hydrosilylation route in their U.S. Pat. No. 2,721,873. That patent specifies the use of a silicon compound having at least one hydrogen attached to the silicon and an unsaturated organic compound containing the unsaturation in a non-benzenoid group to form an organo silicon compound. The silicon compounds utilized may be inorganic or organic. The unsaturated organic compounds include unsaturated hydrocarbons, aliphatic, carbocyclic, alicyclic and heterocyclic compounds including unsaturated alcohols, aldehydes, ketones, quinones, acids, acid anhydrides, esters, nitriles, or nitro compounds. The presence of added catalyst is nonessential, but MacKenzie, et al. say that they may be employed under certain conditions to facilitate reaction or increase yields. MacKenzie, et al. suggest that these catalysts may be selected from compounds and salts in the elements of groups IIIA, IVA, IB and IIB of the periodic system. Group VIII and some of their compounds are suggested as possibilities. Other types of catalysts such as peroxides are indicated and are cited as influencing the direction of addition which takes place.

Prior to this invention, 1,4 addition of silicon hydrides to $\alpha,\beta$-unsaturated carbonyl compounds has been shown to occur in the presence of a homogeneous or soluble catalyst such as tris(triphenylphosphine)rhodium(I) chloride. Since the catalyst is homogeneous, the product must be separated from the catalyst by distillation in order to recover the precious metal.

The process of this invention comprises reacting a hydride of silicon with $\alpha,\beta$-unsaturated esters, ketones or aldehydes in the presence of a heterogeneous noncomplexed rhodium-containing catalyst, that is, a solid catalyst in a gas or liquid system, to make a predominantly 1,4-O-metallation product. After the reaction is complete, the rhodium-containing catalyst can be easily removed by filtration to recover the precious metal. The crude product of this process, after filtration, can be distilled to isolate the 1,4-O-metallation product. In some cases distillation is not required for the product to be useful.

Polymerization inhibitors such as hydroquinone, tetramethyldiphenoquinone, phenothiazine and p-methoxyphenol can be used to retard polymerization of the unsaturated hydrocarbon. These are particularly advantageous when a gaseous hydride such as trimethylsilane is added to a slurry of the $\alpha,\beta$-unsaturated carbonyl compound and the heterogeneous rhodium catalyst.

While the process of this invention can be run neat, the reaction can be run in a solvent such as tetrahydrofuran (THF), ethyl acetate, or ethylene glycol dimethyl ether (glyme). For certain 1,4-O-metallation reactions, fewer impurities in the crude product result when a solvent is employed. Also, the choice of solvent can affect purity.

DETAILED DESCRIPTION OF THE INVENTION

The catalyst employed in this invention is a heterogeneous noncomplexed rhodium-containing catalyst. The degree of reduction of the rhodium can have a significant effect on the activity of the catalyst, with the most highly reduced rhodium exhibiting the least activity. It may be supported by a wide range of substrates including carbon, alumina and silica. The preferred support is carbon. The support chosen can have a significant effect on the rate of reaction.

The hydrides used in this invention are of the structure

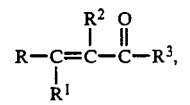

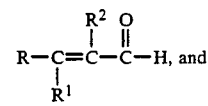

-continued

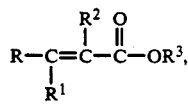

wherein $R^{4a}$, $R^{4b}$ and $R^{4c}$ are the same or different halogen, branched or straight chain alkyl, aralykl or aryl groups. The preferred hydrides are the silicon hydrides, particularly alkylsilanes and principally triethylsilane, trimethylsilane, and methyldiethylsilane.

The α,β-unsaturated carbonyl compounds of this invention are ketones, aldehydes, and esters of the following forms:

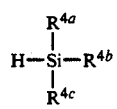

wherein R and $R^1$ can be independently hydrogen, fluoroalkyl or a hydrocarbyl radical which is an aliphatic, allcyclic, aromatic or mixed aliphatic(—) aromatic radical containing up to 20 carbon atoms, optionally containing one or more ether oxygen atoms within the aliphatic or allcyclic segments thereof and optionally containing one or more functional substituents that are unreactive under the conditions of the process. R and $R^1$ can be independently polymeric radicals containing at least 20 carbon atoms and optionally containing one or more oxygen atoms within aliphatic segments thereof and optionally containing one or more functional substituents that are unreactive under the conditions of this process.

$R^2$ and $R^3$ can be independently fluoroalkyl or hydrocarbyl radicals which are aliphatic, alicyclic, aromatic or mixed aliphatic-aromatic containing up to 20 carbon atoms, optionally containing one or more ether oxygen atoms within the aliphatic and allcyclic segments thereof and optionally containing one or more functional substituents that are unreactive under the conditions of this process. $R^2$ and $R^3$ can be independently polymeric radicals containing at least 20 carbon atoms and optionally containing one or more ether oxygen atoms within aliphatic segments thereof and optionally containing one or more functional substituents that are unreactive under the conditions of this process. $R^3$ can also be $(R^4)_3M$ or $R^5$—O—$M(R^4)_3$, where M is silicon; $R^5$ is a branched or straight chain alkyl or alkoxyalkyl having 1 to 20 carbon atoms; and $R^4$ is $R^{4a}$, $R^{4b}$ and $R^{4c}$ as defined in the case of the hydride.

New compositions are produced by the process of this invention when $R^3$ is perfluoroalkyl in above described ester; when $R^2$ is perfluoroalkyl in the above described aidehyde; or when either $R^2$ or $R^3$or both are per fluoroalkyl in the above described ketone.

The α,β-unsaturated esters may also be of the following general structure

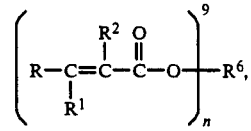

wherein "n" is a whole number of at least 2 and preferably from 2 to 4 and $R^6$ is a branched or straight chain alkyl, alkoxyalkyl, polyalkoxyalkyl, cycloalkyl or aryl group. R, $R^1$, and $R^2$ are as defined above. Esters of this form are reacted to produce 1,4-O-metallation polyfunctional compounds which can be used as polyfunctional initiators in making high molecular weight polymers.

The preferred α,β-unsaturated compounds for making monofunctional initiators for polymer manufacture are the esters of the following form

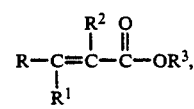

wherein R and $R^1$ are hydrogens, $R^2$ is $CH_3$ and $R^3$ is a branched or straight chain alkyl group from 1 to 8 carbon atoms; fluoroalkyl;

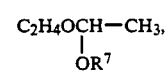

$C_2H_4N(R^7)_2$, wherein $R^7$ is a branched or straight chain alkyl group from 1 to 8 carbons; or $Si(R^4)_3$ or $C_2H_4Si(R^4)_3$, wherein $R^4$ is $R^{4a}$, $R^{4b}$ and $R^{4c}$ as defined above for the hydride.

The most preferred unsaturated esters for producing monofunctional initiators are methyl methacrylate ($R^3$ being $CH_3$), 2(1-ethoxyethoxy) ethyl methacrylate ($R^3$ being

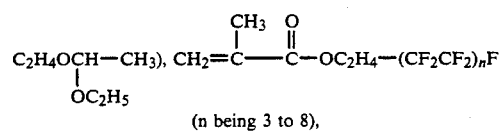

(n being 3 to 8),

2(1-butoxyethoxy) ethyl methacrylate ($R^3$ being

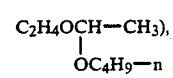

N,N-dimethylaminoethyl methacrylate ($R^3$ being $C_2H_4N(CH_3)_2$), and trialkylsilyl methacrylates ($R^3$ being $Si(C_2H_5)_2CH_3$, $Si(C_2H_5)_3$ or $Si(CH_3)_3$).

The preferred unsaturated esters for producing polyfunctional initiators are ethylene glycol dimethacrylate, butanediol dimethacrylate, trimethylolpropane trimethacrylate and pentaerythritol tetramethacrylate.

Where the hydride is liquid at ambient temperatures as in the case of triethylsilane, a preferred embodiment of the process comprises making a slurry of the heterogeneous rhodium catalyst and the hydride and then slowly adding the α,β-unsaturated carbonyl compound to the slurry. Where the hydride is a gas at ambient temperatures as in the case of trimethylsilane, adding the hydride to a slurry of the catalyst and the α,β-unsaturated carbonyl compound is preferred.

The α,β-unsaturated carbonyl compound to hydride mole ratio preferably should be less than 1:1 but can be greater than 1:1. The preferred percent catalyst concentration (calculated as elemental rhodium) ranges from 0.01 to 0.15 mole percent of the hydride used.

The reaction of this invention is exothermic. Preferred temperatures range from 10° C. to 75° C. and preferred pressures range from atmospheric to 20 psig. The most preferred temperatures and pressures depend on the hydride and the α,β-unsaturated carbonyl compound being reacted. The reaction preferably is carried out in an inert atmosphere since addition of oxygen to the system can cause excessive polymerization of the α,β-unsaturated carbonyl compound.

Polymerization inhibitors may be used and may be preferred where the α,β-unsaturated carbonyl compound is particularly sensitive to polymerization and where the hydride reactivity is low. For example, a polymerization inhibitor would be more preferable in a reaction between trimethylsilane and methyl methacrylate than in the faster reaction of triethylsilane and methyl methacrylate. Preferred polymerization inhibitors are hydroquinone, tetramethyldiphenoquinone phenothiazine and p-methoxyphenol.

Solvents are not required, but can be used. Preferred solvents are THF, ethyl acetate and glyme. Solvent addition can affect yield and purity of the desired 1,4-O-metallation product.

Other additives such as organic and inorganic acids and bases and salts can affect the rate of reaction. Also, catalyst impurities can affect the reaction.

EXAMPLES

The first ten examples are controls indicative of processes not claimed by this invention. The remaining examples are illustrative of the invention and are not intended to limit it in any way. NMR and gas chromatography were the standard laboratory procedures used to identify the product and determine yield and purity. In all examples the weight percent purity assumes that the gas chromatograph·area percent for a compound equals the weight percent of that compound in the sample. The percent crude yield is calculated by means of the following equation:

$$\text{Percent Crude Yield} = \frac{\text{Weight of Filtrate} \times \text{Wt. \% Purity}}{\text{Theoretical Weight of 1,4-O-silylated Product (i.e., 100\% yield assumed)}}$$

EXAMPLES 1 AND 2

The first two examples employ a soluble catalyst, tris(triphenylphosphine)rhodium(I) chloride, in a reaction between methyl methacrylate (MMA) and triethylsilane (TES). In Example 1 a 10 mole percent excess of TES is used; in Example 2 a 50 mole percent excess of MMA is used. In both examples 0.2 gram of catalyst (about 0.1 mole percent) was added to a solution of TES and MMA in a clean, dry flask under a nitrogen atmosphere. In Example 1, 20 grams of MMA and 25.6 grams of TES were used. In each case the mixture was then heated to 55° to 65° C. and held at that temperature and agitated for 25 hours.

In Example 1 a mixture of compounds resulted. The crude yield of the 1,4-O-silylated product,

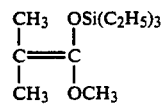

was about 30 percent with a purity of 40.4 weight percent. A similar product resulted in Example 2. In Example 2, however, the crude yield was about 65.5 percent and the purity was about 58.7 percent. Additionally, in Example 2 a 2.3 gram lump of polymeric material formed. In both Example 1 and Example 2 the tris(triphenylphosphine)rhodium(I) chloride catalyst is homogeneous and thus distillation is necessary to separate it from the reaction mixture to recover the rhodium. See Table I.

EXAMPLES 3 AND 4

Examples 3 and 4 both use 1 gram of 5 percent platinum on carbon as the catalyst. In Example 3 a 10 percent excess of triethylsilane (25.6 grams or 0.22 mole) is reacted with 20 grams (0.2 mole) of methyl methacrylate in a clean, dry flask under a nitrogen atmosphere. In Example 4, 23.3 grams (0.2 mole) triethylsilene is reacted with a 50 percent excess of methyl methacrylate (30 grams or 0.3 mole) in a clean, dry flask under a nitrogen atmosphere. In both examples the triethylsilane and catalyst were charged to a clean, dry flask under a nitrogen atmosphere. The charge was heated to 60° to 65° C. and the methyl methacrylate was added dropwise over about 90 minutes. The mixture was maintained at 60° to 65° C. and agitated for a total of 31 hours and then filtered to remove the catalyst. In both Examples 3 and 4 the reaction product was principally the 1,2-β-silylated product of triethylsilane to methyl methacrylate. See Table I.

EXAMPLES 5 AND 6

Using the same procedure as in Examples 3 and 4 one gram of nickel/Kieselguhr catalyst was used in these examples. Example 5 was run with a 10 percent excess of triethylsilane (25.6 grams or 0.22 mole) and 20 grams (0.2 mole) of methyl methacrylate. Example 6 was run with a 50 percent excess of methyl methacrylate (30 grams or 0.3 mole) and 23.3 grams (0.2 mole) of triethyleilane. In both examples the methyl methacrylate was added dropwise over about 100 minutes and the charge was then maintained at 60° to 65° C. and agitated for about 26 hours. No reaction was observed in either case. Anhydrous nickel chloride in the amount of 0.1 gram was then added to the charge in each case. After an additional seven hours at 60° to 65° C. there was still no reaction. See Table I.

EXAMPLES 7, 8, 9 AND 10

Following the same procedure as in Examples 3 through 6 the catalyst in each of these examples was added to the triethylsilane and a 50 percent excess of methyl methacrylate was added dropwise over a 60 to 100 minute time period. In Example 7 one gram of 5 percent palladium on carbon was used as the catalyst. The charge was heated to 60° to 65° C. and maintained at that temperature and agitated for about 32 hours. In Example 8 the catalyst was one gram of 5 percent ruthenium on carbon. The mixture was heated to 60° to 65° C. and maintained at that temperature and agitated for about 18 hours. In Example 9 the catalyst was one gram cobalt on Kieselguhr. In this case the charge was agitated for about 18 hours at 20° to 25° C. and then was heated to 60° to 65° C. and agitated for about 12 ½ hours. In Example 10 the catalyst was one gram of 5 percent iridium on carbon. The charge was agitated at 20° to 25° C. for one hour and then the temperature was elevated to 60° to 65° C. and the charge was agitated for 22 hours. No reaction was observed in Example 9. In the other examples, principally 1,2-β-silylation product, substantial amounts of the starting materials and polymerized MMA resulted. See Table I.

TABLE I

Hydrosilylation of Methyl Methacrylate (MMA) with Triethylsilane (TES)

| Example | Catalyst | Temp. °C. | Time Hrs. | G.C. % Composition 1,2-β- Silylation | G.C. % Composition 1,4-O- Silylation | Comments |
|---|---|---|---|---|---|---|
| 1 | [φ$_3$P]$_3$RhCl | 55–60 | 25 | 16.4 | 40.4 | 10% excess TES Some MMA polymerization |
| 2 | [φ$_3$P]$_3$RhCl | 55–60 | 25 | 1.6 | 58.7 | 50% excess MMA Some MMA polymerization |
| 3 | 5% Pt/C | 60–65 | 31 | 61.8 | 0.3 | 10% excess TES |
| 4 | 5% Pt/C | 60–65 | 31 | 40.9 | 0.8 | 50% excess MMA |
| 5 | Ni/Kieselguhr + NiCl$_2$ | 60–65 | 26 +7 | 0 0 | 0 0 | 10% excess TES No detectable silylated products |
| 6 | Ni/Kieselguhr + NiCl$_2$ | 60–65 | 26 +7 | 0 0 | 0 0 | 50% excess MMA No detectable silylated products |
| 7 | 5% Pd/C | 60–65 | 23 | 8.5 | <0.1 | Further heating resulted in MMA polymerization |
| 8 | 5% Ru/C | 60–65 | 18 | 11.0 | 0.3 | Considerable polymer formation |
| 9 | Co/Kieselguhr | 60–65 | 12 | 0 | 0 | No detectable silylated products |
| 10 | 5% Ir/C | 60–65 | 22 | 18.0 | 0.3 | Considerable polymer formation |

EXAMPLES 11 THROUGH 17

Using a procedure similar to that employed in Examples 3 through 10 the catalyst in each of these examples was added to the triethylsilane (TES) and the ester was added dropwise over a 60 to 75 minute time period. In Examples 11 through 14 a 50 percent excess of methyl methacrylate (MMA) was added. In Example 15 a 10 percent excess of MMA was added. In Examples 16 and 17 a 10 percent excess of 2 (1-ethoxyethoxy) ethyl methacrylate (EEEM) (see U.S. Pat. No. 3,530,167) vacuum stripped of volatiles was used. When the ester was added in each of the examples, an exothermic reaction resulted. In Example 11 one gram of 5 percent rhodium on carbon was used as the catalyst. The reaction mixture was maintained at 60° to 65° C. and agitated after the addition of MMA for 1 ¼ hours. In Example 12 the catalyst was one gram of 5 percent rhodium on carbon. The temperature of the charge was maintained at 20° to 25° C. by means of an ice water bath and was agitated for 22 hours after the addition of MMA was complete. In Example 13, 0.1 gram of 5 percent rhodium on carbon was used and the temperature of the mixture was maintained at 20° to 25° C. while agitating for 24 hours following addition of the MMA. In Example 14, 0.1 gram of 5 percent rhodium on alumina was used and the mixture was maintained at 20° to 25° C. while agitating for 26 hours following addition of the MMA and then was heated to 60° to 65° C. for an additional four hours. In Example 15, 0.5 gram of 1 percent rhodium on carbon was used and the mixture was maintained at 30° to 35° C. while agitating for about four hours after the addition of MMA was complete. In Example 16, 0.5 gram of one percent rhodium on carbon was used and the mixture was maintained at 30° to 35° C. while agitating for about four hours following addition of the EEEM. In Example 17, 0.5 gram of 5 percent rhodium on carbon was used and the mixture was maintained at 30° to 35° C. while agitating for about 2 ½ hours after the addition of EEEM was complete.

In each example the catalyst was removed by filtration and the filtrate was analyzed. In each case a 1,4-O-silylated product resulted. In Examples 11 through 15 that product was of the form,

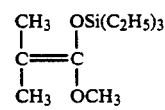

In Examples 16 and 17 the 1,4-O-silylated product was of the form,

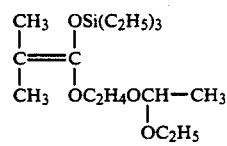

The approximate crude yield and purities are indicated in Table II.

TABLE II

| Example | Catalyst | Silane | α,β- Unsaturated Ester | 1,4-O-Silylation Crude Yield % Theory | 1,4-O-Silylation Purity Wt. % |
|---|---|---|---|---|---|
| 11 | Rh/C | TES | MMA | 71 | 77 |
| 12 | Rh/C | TES | MMA | 52 | 47 |
| 13 | Rh/C | TES | MMA | 65 | 58 |
| 14 | Rh/Alumina | TES | MMA | 74 | 72 |
| 15 | Rh/C | TES | MMA | 85 | 87 |
| 16 | Rh/C | TES | EEEM | 94 | 93 |
| 17 | Rh/C | TES | EEEM | 93 | 94 |

EXAMPLES 18 THROUGH 21

In each of the following examples methyl methacrylate was reacted in the presence of a rhodium-on-carbon catalyst with silanes other than triethylsilane. The weight percent 1,4-O-silylated product (purity) in the filtrate from each of the reactions as well as the percent crude yield for each of the examples is set forth in Table III.

In Example 18 a 10 percent excess of methyl methacrylate (33 grams or 0.33 mole) and 0.2 gram of 5 percent rhodium on carbon were charged to a clean, dry 100-ml Hastelloy C shaker bomb. Then 22.3 grams (0.3 mole) trimethylsilane (TMS) was condensed into the charge. The charge was heated slowly to 35° to 45° C. and held at that temperature for two hours. After cooling the reaction mixture was filtered to remove the catalyst and the liltrate was analyzed. The 1,4-O-silylated product of this example has the following form:

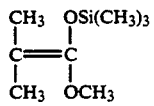

In Example 19, 16.6 grams (0.22 mole) trimethylsilane was added over about 4 ½ hours to a slurry of 0.5 gram 5 percent rhodium on carbon in 20 grams (0.2 mole) methyl methacrylate, 0.0041 gram hydroquinone and 20 ml dry tetrahydrofuran (THF). The reaction mixture was agitated in a four-necked glass flask at 35° to 39° C. for about 1 ½ hours. The system was maintained at about 3 psig during TMS addition by means of a six inch mercury pressure relief column attached to the flask and subsequently as needed by nitrogen addition. The catalyst was filtered off and the filtrate was analyzed. The 1,4-O-silylated product was the same form as in Example 18.

In Example 20 a 50 percent excess of methyl methacrylate (30 grams or 0.3 mole) was added dropwise over 60 minutes to a mixture of 0.1 gram 5 percent rhodium-on-carbon catalyst and 27.3 grams (0.2 mole) phenyldimethylsilane in a clean, dry flask under a nitrogen atmosphere. After the addition was complete the temperature was maintained at 20° to 25° C. for 24 hours. The charge was filtered to remove the catalyst and the filtrate was analyzed. The 1,4-O-silylated product of this example had the form,

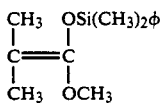

In Example 21 a 5 percent excess of methyl methacrylate (31.5 grams or 0.315 mole) was added dropwise over a 60 minute period to a slurry of 0.5 gram one percent rhodium on carbon in 30.7 grams (0.3 mole) of methyldiethylsilane (MDES) at 30° to 35° C. in a clean, dry flask under a nitrogen atmosphere. After the addition was complete, the charge was allowed to agitate at 30° to 35° C. for about 11 ½ hours. The charge was cooled and filtered to remove the catalyst and the liltrate was analyzed. The 1,4-O-silylated product of this example is of the form,

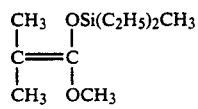

The 1,4-O-silylated product crude yields and purities for Examples 18 through 21 can be found in Table III which follows.

TABLE III

| Example | Catalyst | Silane | α,β-Unsaturated Ester | 1,4-O-Silylation Crude Yield % Theory | Purity Wt. % |
|---|---|---|---|---|---|
| 18 | Rh/C | TMS | MMA | 45 | 49 |
| 19* | Rh/C | TMS | MMA | 70 | 51 |
| 20 | Rh/C | PDMS | MMA | 71 | 81 |
| 21 | Rh/C | MDES | MMA | 72 | 86 |

*Hydroquinone and THF added

EXAMPLES 22 AND 23

In Examples 22 and 23 methyl methacrylate was reacted in the presence of a rhodium-on-carbon catalyst with a chlorinated silicon hydride under a nitrogen atmosphere. The crude product was not analyzed by gas chromatography in either case. Instead, the reaction mixture was filtered to remove the catalyst and the liltrate was distilled. NMR was used to analyze the distillate.

In Example 22 a 50 percent excess of methyl methacrylate (30 grams or 0.3 mole), 0.5 gram 5 percent rhodium-on-carbon catalyst, and 18.9 grams (0.3 mole) distilled dimethylchlorosilane were charged to a 100-ml Hastelloy C shaker bomb and heated at 100° to 110° C. for one hour. The reaction mixture was filtered to remove the catalyst. Distillation of a 35.5 gram sample of the reaction mixture yielded 7.5 grams of a product with a boiling point of 34°-36° C. at 1.4 to 2.0 mm mercury. The NMR analysis of this product was consistent with the following structure:

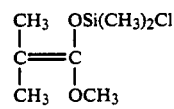

In Example 23 a 50 percent excess of methyl methacrylate (30 grams or 0.3 mole), 0.5 gram of 5 percent rhodium-on-carbon catalyst and 23 grams (0.2 mole) of distilled methyldichlorosilane were charged to a 100-ml Hastelloy C shaker bomb and heated to 85° to 95° C., held at that temperature for half an hour and then heated to 110° to 115° C. at which temperature the mixture was held for one hour. The reaction mixture was filtered to remove the catalyst. Distillation of a 40.2 gram sample of the reaction mixture yielded about 5.7 grams of a product with a boiling point of 33° to 37° C. at 1.5 to 1.6 nun mercury. NMR analysis of the sample indicated that it was a 1:1 molar mixture of 1,4-O-silylated and 1,2-α-silylated products of the respective forms;

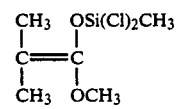

and

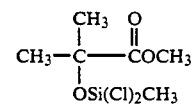

EXAMPLE 24

In this example 30.7 grams (0.3 mole) methyldiethylsilane and 0.5 gram of one percent rhodium on carbon were mixed in a dry, three-necked glass flask. The mixture was deoxygenated by bubbling nitrogen slowly through the mixture for one hour at approximately 25° C. A 10 percent excess of 2(1-butoxyethoxy)ethyl methacrylate (BEEM) (76 grams or 0.33 mole) was then added dropwise to the mixture over a 60 minute period at 30° to 35° C. The charge was agitated for six hours at 30° to 35° C. After filtering to remove the catalyst, the clear filtrate was analyzed. The 1,4-O-silylated product of this example had the form,

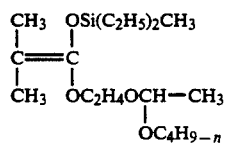

The purity (percent 1,4-O-silylated product in the filtrate) was 82 weight percent. The crude yield of the 1,4-O-silylated product was about 78 percent.

EXAMPLE 25

In this example 31.4 grams (0.2 mole) 2-dimethylaminoethyl methacrylate was added dropwise over about one hour to a slurry of 0.5 gram of 5 percent rhodium on carbon in 21.5 grams (0.21 mole) methyldiethylsilane and 25 ml dry ethyl acetate. The reaction mixture was agitated in a three-necked glass flask at 30° to 35° C. for about one hour. After catalyst filtration, the filtrate was analyzed. The 1,4 -O-silylated compound formed was

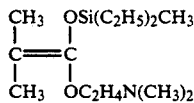

The purity was about 65 weight percent and the yield was about 87 percent of theory.

EXAMPLE 26

In this example 29.7 grams (0.15 mole) ethylene glycol dimethacrylate was added dropwise over a 60 minute period to a mixture of 0.5 gram 5 percent rhodium on carbon and 32.2 grams (0.315 mole) methyldiethylsilane at 30° to 35° C. After the addition was complete, the charge was agitated at 30° to 35° C. for four additional hours. After cooling the charge was filtered to remove the catalyst and the filtrate was analyzed. The 1,4-O-silylated product of this example had the form

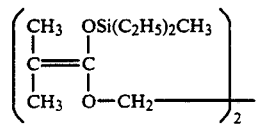

The purity (weight percent of the bis-1,4-O-silylated product in the filtrate) was about 68 weight percent. The yield of the product was about 65 percent of theory.

EXAMPLE 27

Ethylene glycol dimethacrylate (29.7 g, 0.15 mole) was added dropwise (1 hr.) to a mixture of 0.5 g 1% Rh/carbon and 32.2 g (0.35 mole) methyldiethylsilane at 30° to 35° C. After addition of the dimethylsilane was complete, the charge was allowed to agitate at 30° to 35° C. for 4 hrs. The charge, which appeared to contain some polymeric material, was filtered (Super Cel/paper) to give 38 g of a slightly thick cloudy filtrate. The purity of the resulting 1,4-O-silylated product was 64% and the crude yield was 40%. It can be represented by formula:

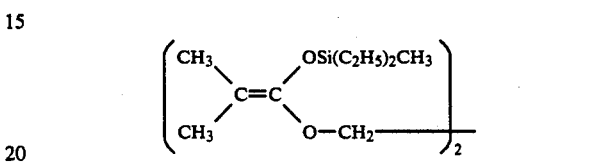

EXAMPLE 28

The procedure for this 1,4-O-silylation was similar to that described in EXAMPLE 19 except that the trimethylsilane was purified by passing it through a column of soda lime. Trimethylsilane (7.6 g, 0.12 mole) was fed (1 ½ hrs.) to a slurry of 0.3 g, 5% Rh/carbon in ethyleneglycol dimethylacrylate (purified through basic alumina) (23.8 g, 0.12 mole), 20 ml of dry ethyl acetate and 0.0165 g of hydroquinone at 35° to 39° C. and 3 psig. After the addition of the dimethacrylate was complete, the charge was allowed to agitate at 35° to 39° C. for 1 hr. The charge was cooled, filtered through Super Cel and paper to give 43.1 g of a clear, colorless liquid. The purity of the resulting 1,4-O-silylated product was 27% and the crude yield was 36%. It is of the formula:

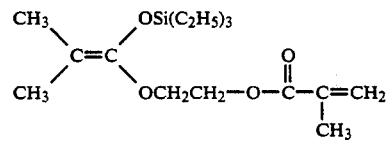

EXAMPLE 29

Ethyl vinyl ether (180.3 g, 2.5 mole), hydroquinone (1.0 g) and trifluoracetic acid (1.8 ml) were charged to a 1000 ml flask under a $N_2$ atmosphere. The charge was warmed to reflux (29° C.) and 260.3 g (2.0 moles) of hydroxyethyl methacrylate (HEMA) was added dropwise (1 hr.) while allowing the temperature to rise to 40±2° C. About 30 min. into the addition it was necessary to use an ice water bath to maintain the temperature at 40° C. After the addition was complete, the charge was heated at 40±2° C. for 2 hrs. It is suspected that some of the ethyl vinyl ether was lost from the system during the addition because of the poor cooling efficiency of the water condenser. The charge was subjected to distillation by heating slowly from 30° C. to 70° C. for 1 hr. A total of 25.1 g of distillate was removed under vacuum and to leave 406.2 g of liquid residue. The purity of the resulting blocked HEMA, 2-(1-ethoxyethoxy)ethyl methacrylate, was 90% and the crude yield was 89%. the residue was subjected to distillation and a fraction with a purity of 94% which boiled at 48° to 56° C. at 0.2 to 0.45 mm Hg pressure was used for the following 1,4-o-silylation. It had the formula:

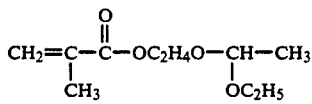

Blocked HEMA (66.8 g, 0.33 mole, prepared as described above) was added dropwise (1 hr.) to a stirred mixture of 0.5 g 5% Rh/carbon in 34.9 g (0.30 mole) of triethylsilane at 30° to 35° C. After 10 ml of blocked HEMA had been added, an exothermic reaction took place and the temperature rose to 51° C. The charge was cooled to 30° to 35° C. with an ice bath. After the addition was complete, the charge was warmed at 30° to 35° C. for 2 ½ hrs. The charge was cooled to 20° C. and the catalyst removed via filtration to give 94.3 g of liquid. The purity of the resulting 1,4-O-silylated product was 94% and the crude yield was 93%. It is of the formula:

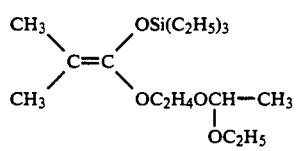

EXAMPLE 30

2-Dimethylaminoethyl methacrylate (31.4 g, 0.2 mole) was added dropwise (1 hr.) to a slurry of 0.5 g 5% Rh/carbon in methyldiethylsilane (21.5 g, 0.21 mole) and 25 ml of dry ethyl acetate at 30° to 35° C. After the addition was complete, the charge was allowed to agitate at 30° to 35° C. for 1 hr. The charge was filtered (Super Cel and paper) to give as a product 69.3 g of clear light yellow filtrate. The purity of the resulting 1,4-O-silylated product was 65% and the crude yield was 87%. It is of the formula:

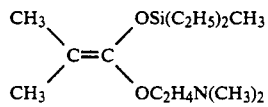

EXAMPLE 31

Hydroxyethyl methacrylate (HEMA) (97.6 g, 0.75 mole) was added dropwise over 1 hr. to a mixture of 82.6 g (0.825 mole) of butyl vinyl ether, 0.38 g of hydroquinone and 0.68 ml of trifluoroacetic acid at 35° to 40° C. After the addition was complete, the charge was allowed to agitate at 40°±2° C. for 2 hrs. The reaction mixture was vacuum (20 mm Hg) stripped at 60° to 65° C. for 2 hrs. to leave 176 g of liquid. The purity of the resulting blocked HEMA 2-(1-butoxyethoxy)ethyl methacrylate was 87% and the crude yield was 89%. It had the formula:

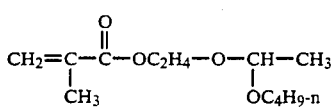

A mixture of 30.76 g of methyldiethylsilane (0.3 mole) and 0.5 g of 1% Rh/carbon was deoxygenated by bubbling $N_2$ slowly through the mixture for 1 hr. at 25° C. Blocked HEMA (76 g, 0.33 mole, prepared as described above) was added dropwise to the mixture over a period of 1 hr. at 30° to 35° C. the mixture was slightly exothermic throughout the entire addition of blocked HEMA. The charge was then allowed to agitate at 30° to 35° C. for 6 hrs. The charge was filtered (Super Cel and paper) to give as a product 95 g of a clear filtrate. The purity of the resulting 1,4-O-silylated product was 82% and the crude yield was 78%. It had the formula:

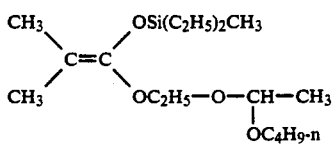

EXAMPLE 32

2-Methyl-2-pentenal (19.6 g, 0.2 mole) was added dropwise (1 hr.) to a slurry of 0.5 g 5% Rh/carbon in (25.6 g, 0.22 mole) triethylsilane and 20 ml of dry ethyl acetate at 30° to 35° C. After ½ of the 2-methyl-2-pentenal had been added, there was an exothermic reaction causing the temperature to increase from 35° C. to 80° C. The charge was cooled back to 30° to 35° C. by means of an ice bath and the addition completed. The charge was heated at 35°±2° C. for 8 hrs., and then filtered to give 50.1 g of a clear, slightly amber liquid. The purity of the resulting 1,4-O-silylated product was 61% and the crude yield was 71%. It had the formula:

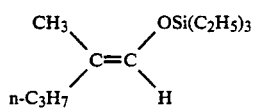

EXAMPLE 33

1-Acetyl-1-cyclohexene (24.8 g, 0.2 mole) was added dropwise (1 ½ hrs.) to a slurry of 0.5 g 5% Rh/carbon in triethylsilane (25.6 g, 0.22 mole and 20 ml dry ethyl acetate. The first (½) of the addition was carried out at 30° to 35° C. The addition was stopped and the temperature increased to 50° to 55° C. by external heating. The remainder of the addition was carried out at 50° to 55° C. After the addition was complete, the charge was warmed at 50° to 55° C. for 4 hrs. During the heating period, the reaction mixture became exothermic and it was necessary to use a cooling bath to maintain the temperature at 50° to 55° C. The charge was cooled to 25° C. and filtered to give 61.7 g of a clear, amber liquid. The purity of the resulting 1,4-O-silylated product was 37% and the crude yield was 48%. It is of the formula:

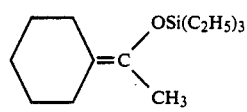

EXAMPLE 34

The procedure for this preparation was similar to that described in EXAMPLE 19 except that the trimethylsilane was purified by passing it through a column of soda lime. Trimethylsilane (16.2 g, 0.22 mole) was fed (3 ¼ hrs.) to a slurry of 0.5 5% Rh/carbon in butyl methacrylate (28.4 g, 0.2 mole) 20 ml ethylacetate and 0.0042 g hydroquinone at 35° to 39° C. (The butyl methacrylate and ethylacetate for this experiment were each dried by passing them through a column of 4A molecular sieves from Davison Chemical.) After the addition of TMS was complete, the charge was allowed to agitate at 35° to 39° C. for 2 hrs. The charge was cooled to 20° C. and the pressure vented off. The charge was filtered to give 57.9 g of a clear, colorless filtrate. The purity of the resulting 1,4-O-silylated product was 67% and the crude yield was 89%. It is of the formula:

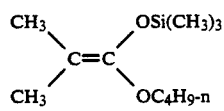

EXAMPLE 35

Benzyldimethylsilane (45 g, 0.3 mole) was added dropwise (1 ½ hrs.) in a slurry of 0.5 g 5% Rh/carbon in 33 g (0.33 mole) methylmethacrylate, 30 ml ethyl acetate and 0.0060 g hydroquinone at 30° to 35° C. in a $N_2$ atmosphere. After addition of benzyldimethylsilane was complete, the charge was allowed to agitate to 30° to 35° C. for 2 hrs. The charge was warmed to 60° to 65° C. and heated at 60° to 65° C. for 6 hrs. The charge was filtered through paper to give 90.0 g of a brownish, colored filtrate. The purity of the resulting 1,4-O-silylated product was 36% and the crude yield was 44%. It is of the formula:

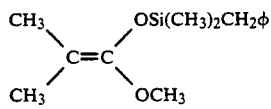

What is claimed is:

1. A process for the production of a predominantly 1,4-O-metallation product which comprises reacting a silicon hydride, of the formula:

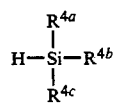

halogen branched or straight chain alkyl, aralkyl or aryl groups, with an α,β-unsaturated carbonyl compound in the presence of a heterogeneous noncomplexed rhodium containing catalyst.

2. The process of claim 1 wherein the silicon hydride is an alkyl silane.

3. The process of claim 1 wherein the α,β-unsaturated carbonyl compound is an ester having the structure

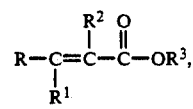

wherein R and $R^1$ are selected independently from the group consisting of hydrogen and alkyl, aryl, cycloalkyl and mixed alkyl-aryl radicals containing 1 to 20 carbon atoms, $R^2$ and $R^3$ are selected from the group consisting of branched or straight chain alkyl radicals having 1 to 20 carbon atoms, fluoroalkyl, aryl, benzyl, cycloalkyl, furfuryl, tetrahydrofurfuryl, chloroalkyl, cyanoalkyl, substituted aminoalkyl, alkoxyalkyl, polyalkoxyalkyl, and phenoxyalkyl radicals and $R^3$ further being selected from the group consisting of $(R4)_3M$ and $R^5-O-M(R^4)_3$, wherein M is silicon, germanium, or tin and $R^5$ is a divalent branched or straight chain alkyl or alkoxyalkyl radical having 1 to 20 carbon atoms and $R^4$ is selected from the group consisting of hydrogen, halogens, and branched or straight chain alkyl, aryl, alkoxy, and benzyl radicals having from 1 to 20 carbon atoms.

4. The process of claim 1 wherein the α,β-unsaturated carbonyl compound is an ester having the structure

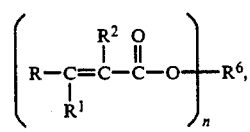

wherein n is a whole number from 2 to 4 and $R^6$ is at least divalent and is selected from the group consisting of branched or straight chain alkyl, alkoxyalkyl, polyalkoxyalkyl, cycloalkyl, and aryl radicals.

5. The process of claim 3 wherein R and $R^1$ are hydrogen, $R^2$ is $CH_3$, M is silicon, and $R^3$ is a branched or straight chain alkyl group containing from 1 to 8 carbon atoms, fluoroalkyl,

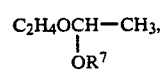

$C_2H_4N(R^7)_2$, $Si(R^4)_3$, or $C_2H_4Si(R^4)_3$ wherein $R^7$ is a branched or straight chain alkyl group having from 1 to 8 carbons.

6. The process of claim 4 wherein the ester is selected from the group consisting of ethylene glycol dimethacrylate, butanediol dimethacrylate, trimethylolpropane trimethacrylate, and pentaertythritol tetramethacrylate.

7. The process of claim 1 wherein the heterogeneous noncomplexed rhodium-containing catalyst is supported on a substrate selected from the group consisting of carbon, alumina, and silica.

8. The process of claim 7 wherein the substrate is carbon.

9. The process of claim 1 comprising the further step of removing the heterogeneous noncomplexed rhodium-containing catalyst by filtration after the reaction step is complete.

10. The process of claim 9 comprising the further step of distillation following the filtration.

11. The process of claim 1 wherein the reaction is run at a temperature from about 10° C. to 75° C. and at a pressure from about atmospheric to 20 psig.

12. The process of claim 1 further comprising running the reaction in the presence of a solvent.

13. The process of claim 12 wherein the solvent is selected from the group consisting of tetrahydrofuran, ethyl acetate, and ethylene glycol dimethyl ether.

14. The process of claim 1 further comprising running the reaction in the presence of a polymerization inhibitor.

15. The process of claim 14 wherein the polymerization inhibitor is selected from the group consisting of hydroquinone, tetramethyldiphenoquinone, phenothiazine, and p-methoxyphenol.

16. The process of claim 1 further comprising running the reaction in an inert atmosphere.

* * * * *